United States Patent
Yang et al.

(10) Patent No.: US 10,220,375 B2
(45) Date of Patent: Mar. 5, 2019

(54) CATALYST FOR FISCHER-TROPSCH SYNTHESIS AND METHOD FOR PREPARING THE SAME, AND METHOD FOR PREPARING MODIFIED MOLECULAR SIEVE CARRIER

(71) Applicant: Wuhan Kaidi Engineering Technology Research Institute Co., Ltd., Wuhan (CN)

(72) Inventors: Weiguang Yang, Wuhan (CN); Qianqian Liu, Wuhan (CN); Dechen Song, Wuhan (CN); Changyuan Li, Wuhan (CN); Xiaodong Zhan, Wuhan (CN); Jiaqi Jin, Wuhan (CN); Yanfeng Zhang, Wuhan (CN)

(73) Assignee: WUHAN KAIDI ENGINEERING TECHNOLOGY RESEARCH INSTITUTE CO., LTD., Wuhan (CN)

( * ) Notice: Subject to any disclaimer, the term of this patent is extended or adjusted under 35 U.S.C. 154(b) by 362 days.

(21) Appl. No.: 14/923,404

(22) Filed: Oct. 26, 2015

(65) Prior Publication Data
US 2016/0045903 A1  Feb. 18, 2016

Related U.S. Application Data

(63) Continuation-in-part of application No. PCT/CN2014/074974, filed on Apr. 9, 2014.

(30) Foreign Application Priority Data

Apr. 25, 2013 (CN) .......................... 2013 1 0147608

(51) Int. Cl.
| | |
|---|---|
| *B01J 29/06* | (2006.01) |
| *B01J 29/85* | (2006.01) |
| *B01J 29/00* | (2006.01) |
| *B01J 29/035* | (2006.01) |
| *B01J 29/072* | (2006.01) |
| *B01J 29/76* | (2006.01) |
| *B01J 29/70* | (2006.01) |
| *B01J 29/78* | (2006.01) |
| *B01J 29/46* | (2006.01) |

(Continued)

(52) U.S. Cl.
CPC ........... *B01J 29/85* (2013.01); *B01J 23/8892* (2013.01); *B01J 29/005* (2013.01); *B01J 29/0356* (2013.01); *B01J 29/0358* (2013.01); *B01J 29/072* (2013.01); *B01J 29/405* (2013.01); *B01J 29/46* (2013.01); *B01J 29/48* (2013.01); *B01J 29/7065* (2013.01); *B01J 29/76* (2013.01); *B01J 29/763* (2013.01); *B01J 29/78* (2013.01); *B01J 29/783* (2013.01); *B01J 37/0201* (2013.01); *B01J 37/0236* (2013.01); *B01J 37/08* (2013.01); *B01J 37/30* (2013.01); *C07C 1/0445* (2013.01); *C10G 2/332* (2013.01); *C10G 2/334* (2013.01); *B01J 2229/186* (2013.01); *B01J 2229/37* (2013.01); *C07C 2523/04* (2013.01); *C07C 2523/08* (2013.01); *C07C 2523/72* (2013.01); *C07C 2523/745* (2013.01); *C07C 2523/889* (2013.01); *C07C 2529/035* (2013.01); *C07C 2529/072* (2013.01); *C07C 2529/076* (2013.01); *C07C 2529/46* (2013.01); *C07C 2529/48* (2013.01); *C07C 2529/76* (2013.01); *C07C 2529/78* (2013.01); *C07C 2529/85* (2013.01)

(58) Field of Classification Search
CPC .. B01J 29/0358; B01J 29/005; B01J 29/0356; B01J 29/035; B01J 29/405; B01J 29/48; B01J 29/85; B01J 29/78; B01J 29/783; B01J 29/072; B01J 29/46; B01J 29/7065; B01J 29/763; B01J 29/76; B01J 2229/37; B01J 2229/186; B01J 37/0201; B01J 37/0236; B01J 37/08; B01J 37/30; C07C 2529/035; C07C 2529/072; C07C 2529/076; C07C 2529/46; C07C 2529/48; C07C 2529/76; C07C 2529/78; C07C 2529/85
USPC ............................................... 502/60, 73, 74
See application file for complete search history.

(56) References Cited

U.S. PATENT DOCUMENTS

| | | | | |
|---|---|---|---|---|
| 2003/0149321 | A1* | 8/2003 | Mees ....................... | B01J 29/85 585/640 |
| 2009/0036296 | A1* | 2/2009 | Hu .......................... | B01J 23/75 502/78 |

FOREIGN PATENT DOCUMENTS

| | | | |
|---|---|---|---|
| CN | 101411988 | * | 4/2009 |
| CN | 102451749 | * | 10/2010 |
| WO | WO 2009/094935 | * | 8/2009 |

OTHER PUBLICATIONS

Machine translation of CN 101411988, Apr. 2009.*
Machine translation of CN 102451749, Oct. 2010.*

* cited by examiner

*Primary Examiner* — Elizabeth D Wood
(74) *Attorney, Agent, or Firm* — Matthias Scholl P.C.; Matthias Scholl

(57) ABSTRACT

A catalyst, including a molecular sieve carrier and an active component. The active component includes: iron, manganese, copper, and a basic promoter potassium. The molecular sieve carrier is a cerium salt and/or praseodymium salt modified-aluminosilicate molecular sieve carrier and/or silica-rich molecular sieve carrier. A method for preparing a catalyst for Fischer-Tropsch synthesis, includes: 1) fully dissolving a ferric salt, a manganese salt, a copper salt, and an alkali or a salt containing potassium element in water to yield an aqueous solution, stirring and adding sodium lauryl sulfate to the aqueous solution, and continuing stirring to yield a uniform solution; and impregnating a modified (Continued)

molecular sieve in the uniform solution to yield a mixed solution; and 2) drying and calcining the mixed solution to yield the catalyst.

3 Claims, No Drawings

(51) Int. Cl.
*B01J 37/30* (2006.01)
*B01J 23/889* (2006.01)
*B01J 29/40* (2006.01)
*B01J 29/48* (2006.01)
*C10G 2/00* (2006.01)
*C07C 1/04* (2006.01)
*B01J 37/02* (2006.01)
*B01J 37/08* (2006.01)

CATALYST FOR FISCHER-TROPSCH SYNTHESIS AND METHOD FOR PREPARING THE SAME, AND METHOD FOR PREPARING MODIFIED MOLECULAR SIEVE CARRIER

CROSS-REFERENCE TO RELATED APPLICATIONS

This application is a continuation-in-part of International Patent Application No. PCT/CN2014/074974 with an international filing date of Apr. 9, 2014, designating the United States, now pending, and further claims priority benefits to Chinese Patent Application No. 201310147608.2 filed Apr. 25, 2013. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND OF THE INVENTION

Field of the Invention

The invention relates to a catalyst for Fischer-Tropsch synthesis and a method for preparing the same, and a method for preparing a modified molecular sieve carrier.

Description of the Related Art

Typically, light olefins are prepared by one-step Fischer-Tropsch synthesis, but the produced light olefins often are formed with low selectivity. The low selectivity restricts commercial scale production of light olefins by the Fischer-Tropsch synthesis.

Molten iron is a typical catalyst for improving the selectivity of light olefins. However, molten iron has poor mechanical performance and often results in blockage of the catalyst bed or scale formation. This decreases the production efficiency.

SUMMARY OF THE INVENTION

In view of the above-described problems, it is one objective of the invention to provide a catalyst for Fischer-Tropsch synthesis and a method for preparing the same, and a method for preparing a cerium salt and/or praseodymium salt modified-molecular sieve carrier. The preparation methods of the invention are applicable for industrialization and the prepared catalyst has high catalytic activity and reliable stability.

To achieve the above objective, in accordance with one embodiment of the invention, there is provided a catalyst for Fischer-Tropsch synthesis. The catalyst comprises a molecular sieve carrier and an active component. The molecular sieve carrier is a cerium salt and/or praseodymium salt modified-aluminosilicate molecular sieve carrier and/or silica-rich molecular sieve carrier.

In a class of this embodiment, the active component comprises: iron as a primary component, manganese, copper, and a basic promoter. The basic promoter is potassium. The catalyst comprises: between 10 and 35 wt. % of iron, between 1 and 20 wt. % of manganese, between 1 and 20 wt. % of copper, between 1 and 10 wt. % of potassium, and between 40 and 80 wt. % of the molecular sieve carrier.

In a class of this embodiment, the cerium salt and/or the praseodymium salt account(s) for between 1 and 20 wt. % of the cerium salt and/or the praseodymium salt modified-molecular sieve carrier.

In a class of this embodiment, the cerium salt and/or the praseodymium salt account(s) for between 10 and 20 wt. % of the cerium salt and/or the praseodymium salt modified-molecular sieve carrier.

In accordance with another embodiment of the invention, there is provided a method for preparing a cerium salt and/or praseodymium salt modified-molecular sieve carrier. The method comprises:

1) adding an aluminosilicate molecular sieve SSZ-13 and/or SAPO-34 and/or silica-rich molecular sieve ZSM-5 to one acid solution selected from the group consisting of ammonium sulfate, ammonium nitrate, ammonium chloride, acetic acid, and refluxing a resulting mixture at a temperature of between 26 and 99° C. for between 3 and 6 hrs, in which a concentration of the acid solution is between 0.05 and 5 mol/L; filtering a reaction mixture, washing and drying a filter residue, and calcining the filter residue at a temperature of between 400 and 700° C. for between 1 and 8 hrs, whereby yielding a hydrogen type-molecular sieve;

2) impregnating the hydrogen type-molecular sieve obtained in 1) in a cerium salt and/or praseodymium salt solution having a concentration of between 0.1 and 1 mol/L at a temperature of between 25 and 85° C. and a vacuum degree of between $10^{-1}$ and $10^{-4}$ pascal for between 15 and 30 hrs; and 3) drying an impregnated molecular sieve obtained in 2) at a temperature of between 70 and 150° C. for between 15 and 30 hrs, and calcining a resulting product at a temperature of between 400 and 700° C. for between 1 and 8 hrs, whereby yielding the cerium salt and/or the praseodymium salt modified-molecular sieve.

In a class of this embodiment, the cerium salt or the praseodymium salt is a carbonate or a formate.

In a class of this embodiment, a drying temperature of the modified molecular sieve is between 80 and 130° C., and a drying time of the modified molecular sieve is between 20 and 30 hrs. A calcining temperature of the modified molecular sieve is between 500 and 700° C., and a calcining time of the modified molecular sieve is between 4 and 8 hrs.

In accordance with still another embodiment of the invention, there is provided a method for preparing a catalyst for Fischer-Tropsch synthesis. The method comprises:

1) fully dissolving a ferric salt, a manganese salt, a copper salt, and an alkali or a salt containing potassium element according to the following weight percentages: between 10 and 35 wt. % of iron, between 1 and 20 wt. % of manganese, between 1 and 20 wt. % of copper, and between 1 and 10 wt. % of potassium in a definite quantity of an aqueous solvent to yield an aqueous solution, adding a certain weight of a surfactant sodium lauryl sulfate to the aqueous solution while stirring, and continuing stirring to yield a uniform solution; and impregnating a cerium salt and/or the praseodymium salt modified-molecular sieve in the uniform solution to yield a mixed solution under a vacuum degree of between $10^{-1}$ and $10^{-4}$ pascal; and 2) drying the mixed solution at a temperature of between 30 and 70° C. for between 1 and 8 hrs, and calcining a dried composition at a temperature of between 400 and 600° C. for between 3 and 8 hrs, whereby yielding the catalyst.

In a class of this embodiment, the ferric salt is ferric nitrate, ferric oxalate, or ferric citrate. The manganese salt, the copper salt, or the salt of the alkali metal promoter is an oxalate, an acetate, or a carbonate.

In a class of this embodiment, a drying temperature of the mixed solution in 2) is between 50 and 65° C., and a drying time of the mixed solution is between 6 and 8 hrs. A calcining temperature of the mixed solution in 2) is between 500 and 600° C., and a calcining time of the mixed solution is between 6 and 8 hrs.

In a class of this embodiment, the weight percentages in 1) are as follows: between 10 and 35 wt. % of iron, between 1 and 10 wt. % of manganese, between 1 and 10 wt. % of copper, and between 1 and 10 wt. % of potassium. The modified molecular sieve accounts for between 60 and 80 wt. % of the catalyst.

Advantages of the catalyst for Fischer-Tropsch synthesis according to embodiments of the invention are summarized as follows.

The modification of the carrier is simple and convenient and decreases the production cost. The catalyst of the invention is prepared by impregnation, which reduces the energy consumption compared to the molten iron catalyst necessitated to be prepared in a high temperature furnace. The preparation process of the invention is simple and easy for industrialization.

The catalytic activity and the stability of the catalyst are obviously improved in the Fischer-Tropsch reaction for synthesizing olefin. The conversion rate of CO reaches 93%, both the selectivity of light olefin and the ratio of olefin to alkane are improved, and the light olefin accounts for 85 wt. % of $C_2$-$C_4$ hydrocarbons. In addition, the selectivity of methane is inhibited.

DETAILED DESCRIPTION OF THE EMBODIMENTS

For further illustrating the invention, experiments detailing a catalyst for Fischer-Tropsch synthesis and a method for preparing the same, and a method for preparing a cerium salt and/or praseodymium salt modified-molecular sieve carrier are described below. It should be noted that the following examples are intended to describe and not to limit the invention.

A molecular sieve carrier of a catalyst for Fischer-Tropsch synthesis for preparation of light olefin using syngas is a cerium and/or praseodymium modified-aluminosilicate molecular sieve (SSZ-13, SAPO-34), a silica-rich molecular sieve (ZSM-5), or a mixture thereof.

A method for preparing the modified molecular sieve comprises the following steps:

1) adding an aluminosilicate molecular sieve SSZ-13 and/or SAPO-34 or a silica-rich molecular sieve ZSM-5 to one acid solution selected from the group consisting of ammonium sulfate, ammonium nitrate, ammonium chloride, acetic acid, and refluxing a resulting mixture at a temperature of between 26 and 99° C. for between 3 and 6 hrs, in which a concentration of the acid solution is between 0.05 and 5 mol/L; filtering a reaction mixture, washing and drying a filter residue, and calcining the filter residue at 700° C. for 6 hrs to yield a hydrogen type-molecular sieve;

2) fully mixing the hydrogen type-molecular sieve obtained in 1) with a cerium salt (or a praseodymium salt) solution having a concentration of between 0.1 and 1 mol/L for impregnating the hydrogen type molecular at a temperature of between 25 and 85° C. and a vacuum degree of between $10^{-1}$ and $10^{-4}$ pascal for between 15 and 30 hrs; and 3) drying an impregnated molecular sieve obtained in 2) at a temperature of between 70 and 150° C. for between 15 and 30 hrs, and calcining a resulting product at a temperature of between 400 and 700° C. for between 1 and 8 hrs, whereby yielding the cerium salt (or the praseodymium salt)-modified molecular sieve.

The cerium salt (or the praseodymium salt) accounts for between 1 and 20 wt. %, and preferably between 10 and 20 wt. %, of the modified molecular sieve.

The cerium salt (or the praseodymium salt) is a nitrate, a formate, a carbonate, or a sulfate thereof; preferably the carbonate or the formate thereof.

The drying temperature of the modified molecular sieve is between 70 and 150° C., and preferably between 80 and 130° C. The drying time of the modified molecular sieve is between 15 and 30 hrs, and preferably between 20 and 30 hrs.

The calcining temperature of the modified molecular sieve is between 400 and 700° C., and preferably between 500 and 700° C. The calcining time of the modified molecular sieve is between 1 and 8 hrs, and preferably between 4 and 8 hrs.

The catalyst for Fischer-Tropsch synthesis comprises: a primary component comprising iron, an active component comprising manganese and copper, a basic promoter, and a structure promoter. The basic promoter is potassium. The structure promoter is selected from the group consisting of cerium (or praseodymium) modified-SSZ-13, SAPO-34, ZSM-5, and a mixture thereof.

The catalyst of the invention can be prepared by the common preparation method in the technical field, and preferably by the impregnation method.

A method for preparing the catalyst of the invention comprises the following steps:

1) preparing the cerium (or praseodymium) modified-molecular sieve;

2) dissolving a ferric salt, a manganese salt, a copper salt, and an alkali or a salt containing potassium element according to a certain weight ratio in a definite quantity of an aqueous solvent to yield an aqueous solution, adding a certain weight of a surfactant to the aqueous solution while stirring, and continuing stirring to yield a uniform solution; and impregnating the modified molecular sieve prepared in 1) in the uniform solution at a vacuum degree of between $10^{-1}$ and $10^{-4}$ pascal to yield a mixed solution;

3) drying the mixture at a temperature of between 30 and 70° C. for between 1 and 8 hrs, and calcining a dried composition at a temperature of between 400 and 600° C. for between 3 and 8 hrs to yield the catalyst.

The ferric salt is ferric nitrate, ferric oxalate, ferric citrate, or ferric sulfate, and preferably ferric nitrate, ferric oxalate, or ferric citrate.

The manganese salt, the copper salt, or the salt of the alkali metal promoter is an oxalate, an acetate, a citrate, a nitrate, a sulfate, or a carbonate, and preferably the oxalate, the acetate, or the carbonate thereof.

The drying temperature of the mixed solution is between 30 and 70° C., preferably between 50 and 65° C.; and a drying time of the mixed solution is between 3 and 8 hrs, preferably between 6 and 8 hrs. The calcining temperature of the mixed solution is between 400 and 600° C., preferably between 500 and 600° C.; and a calcining time of the mixed solution is between 3 and 8 hrs, preferably between 6 and 8 hrs.

The weight percentages of relative components of the catalyst are as follows: between 10 and 35 wt. % of iron, between 1 and 10 wt. % of manganese, between 1 and 10 wt. % of copper, between 1 and 10 wt. % of potassium, and between 40 and 80 wt. % of the molecular sieve carrier.

Preferably, the weight percentages in 1) are as follows: between 10 and 35 wt. % of iron, between 1 and 10 wt. % of manganese, between 1 and 10 wt. % of copper, and between 1 and 10 wt. % of potassium; and a preferable ratio of the modified molecular for the benefit of controlling the catalyst is between 60 and 80 wt. %.

A method for using the catalyst in synthesizing the low-carbon olefin using syngas comprises: adding 1 mL of the catalyst to a constant zone of a fixed bed reactor having an inner diameter of 8 mm; reducing the catalyst by introducing hydrogen at a space velocity of 1500 $h^{-1}$ at 380° C. for 8 hrs before reaction; and introducing the syngas having a ratio of hydrogen to carbon of 2 to the reactor at the space velocity of 1000 $^{-1}$ at a pressure of 2 megapascal for reaction.

EXAMPLE 1

Cerium nitrate and an aluminosilicate molecular sieve SSZ-13 were weighed according to a weight ratio of cerium to the molecular sieve of 1:9. The molecular sieve was added to an ammonium nitrate solution having a concentration of 0.1 mol/L and a resulting mixture was refluxed at 80° C. for 5 hrs and then filtered. A filter residue was washed, dried, and calcined at 700° C. for 6 hrs to yield a hydrogen type-molecular sieve. Thereafter, the hydrogen type-molecular sieve was uniformly mixed with a cerium nitrate solution and then impregnated at 85° C. at the vacuum degree of $10^{-4}$ pascal for 24 hrs. The molecular sieve after impregnation was dried at 130° C. for 20 hrs and calcined at 550° C. for 6 hrs so as to obtain a modified molecular sieve.

Ferric oxalate, manganese nitrate, copper citrate, and potassium carbonate were weighed according to a weight ratio of iron:manganese:copper:potassium=28:5:5:5 and dissolved in water to prepare a solution. A surfactant sodium lauryl sulfate having a weight accounting for 0.1 wt. % of a weight of the solution was added to the solution while stirring. The cerium modified-aluminosilicate molecular sieve SSZ-13 was weighed quantitatively according to a weight ratio of iron to the molecular sieve of 7:15. The solution was added to the molecular sieve under vacuum and uniformly mixed to yield a mixture. The mixture was then dried at 65° C. for 4 hrs and calcined at 600° C. for 3 hrs to yield a FTO catalyst A in a powder state, and specific components of the catalyst were listed in Table 1. Thereafter, the FTO catalyst A was shaped by pressing, crushed into particles, and sieved. 1 mL of the catalyst having a particle size of between 30 and 60 meshes was added to the fixed bed reactor. Hydrogen was introduced at a space velocity of 1500 $h^{-1}$ to reduce the catalyst at 380° C. for 8 hrs. Then, the syngas (volume ratio of $H_2$: CO=2:1) was introduced at the space velocity of 1000 $h^{-1}$ at 340° C. and 2.0 megapascal for continuous reaction. Gas-phase products were detected on line every hour by gas chromatography, and C5+, oxygenates, and $CO_2$ were excluded from the product selectivity. The reaction results using the catalyst A were shown in Table 2 from which it was known that a conversion rate of CO was 96.1% and selectivity of the light olefin in light hydrocarbon (excluding methane) was 90.1%.

TABLE 1

Specific components of catalysts A-K

| Catalyst | Compositions of modified carrier by weight percentage | Compositions of catalyst by weight percentage |
|---|---|---|
| A | 10% cerium | 28 iron:5 manganese:5 copper:5 potassium:60 modified molecular sieve |
| B | 5% cerium | 22 iron:6 manganese:5 copper:2 potassium:65 modified molecular sieve |

TABLE 1-continued

Specific components of catalysts A-K

| Catalyst | Compositions of modified carrier by weight percentage | Compositions of catalyst by weight percentage |
|---|---|---|
| C | 1% cerium | 18 iron:6 manganese:3 copper:1 potassium:72 modified molecular sieve |
| D | 20% praseodymium | 39 iron:10 manganese:9 copper:2 potassium:40 modified molecular sieve |
| E | 10% praseodymium | 22 iron:6 manganese:4 copper:2 potassium:66 modified molecular sieve |
| F | 5% praseodymium | 18 iron:6 manganese:3 copper:1 potassium:72 modified molecular sieve |
| G | 0.5% cerium + 0.5% praseodymium | 15 iron:10 manganese:5 copper:5 potassium:65 modified molecular sieve |
| H | 5% cerium + 5% praseodymium | 35 iron:1 manganese:5 copper:4 potassium:55 modified molecular sieve |
| I | 10% cerium + 10% praseodymium | 20 iron:10 manganese:5 copper:2 potassium:63 modified molecular sieve |
| J | 20% cerium | 10 iron:5 manganese:3 copper:2 potassium:80 modified molecular sieve |
| K | 1% praseodymium | 23 iron:1 manganese:9 copper:7 potassium:60 modified molecular sieve |

TABLE 2

Evaluation results of catalyst activity

| Catalyst | Conversion rate of CO (%) | Selectivity (%) | | | Ratio of Light olefin to $C_2$-$C_4$ hydrocarbon |
|---|---|---|---|---|---|
| | | $CH_4$ | $C_2$-$C_4$ alkane | $C_2$=-$C_4$= olefin | |
| A | 96.1 | 10.7 | 8.2 | 74.5 | 90.1 |
| B | 95.6 | 13.1 | 10.5 | 69.8 | 86.9 |
| C | 94.7 | 14.5 | 12.2 | 67.4 | 84.7 |
| D | 94.9 | 12.5 | 9.0 | 71.6 | 88.8 |
| E | 93.3 | 11.7 | 10.1 | 68.5 | 87.2 |
| F | 94.5 | 13.6 | 11.3 | 68.7 | 85.6 |
| G | 95.2 | 13.5 | 9.5 | 73.2 | 88.5 |
| H | 96.3 | 11.1 | 8.6 | 71.5 | 89.3 |
| I | 96.3 | 14.6 | 10.0 | 70.5 | 87.6 |
| J | 95 | 12.5 | 11.5 | 69.4 | 85.8 |
| K | 94.2 | 14.8 | 11.4 | 72.1 | 86.3 |

EXAMPLE 2

Cerium nitrate and an aluminosilicate molecular sieve SSZ-13 were weighed according to a weight ratio of cerium to the molecular sieve of 1:19. The molecular sieve was added to an ammonium sulfate solution having a concentration of 0.1 mol/L and a resulting mixture was refluxed at 80° C. for 5 hrs and then filtered. A filter residue was washed, dried, and calcined at 700° C. for 6 hrs to yield a hydrogen type-molecular sieve. Thereafter, the hydrogen type-molecular sieve was uniformly mixed with a cerium nitrate solution and then impregnated at 25° C. at the vacuum degree of $10^{-1}$ pascal for 30 hrs. The molecular sieve after impregnation was dried at 150° C. for 15 hrs and calcined at 700° C. for 6 hrs so as to obtain a modified molecular sieve.

Ferric nitrate, manganese nitrate, copper nitrate, and potassium nitrate were weighed according to a weight ratio of iron:manganese:copper:potassium=22:6:6:2 and dissolved in water to prepare a solution. A surfactant sodium lauryl sulfate having a weight accounting for 0.1 wt. % of a weight of the solution was added to the solution while stirring. The cerium modified-aluminosilicate molecular sieve SSZ-13 was weighed quantitatively according to a weight ratio of iron to the molecular sieve of 22:65. The solution was added to the molecular sieve under vacuum and uniformly mixed to yield a mixture. The mixture was then dried at 30° C. for 8 hrs and calcined at 500° C. for 5 hrs to yield a FTO catalyst B in a powder state, and specific components of the catalyst B were listed in Table 1. Evaluation process of the activity of the catalyst was the same as that of Example 1. The reaction results using the catalyst B were shown in Table 2 from which it was known that a conversion rate of CO was 95.6% and selectivity of the light olefin in light hydrocarbon (excluding methane) was 86.9%.

EXAMPLE 3

Cerium nitrate and an aluminosilicate molecular sieve SAPO-34 were weighed according to a weight ratio of cerium to the molecular sieve of 1:99. The molecular sieve was added to an ammonium nitrate solution having a concentration of 0.1 mol/L and a resulting mixture was refluxed at 80° C. for 5 hrs and then filtered. A filter residue was washed, dried, and calcined at 700° C. for 6 hrs to yield a hydrogen type-molecular sieve. Thereafter, the hydrogen type-molecular sieve was uniformly mixed with a cerium nitrate solution and then impregnated at 50° C. at the vacuum degree of $10^{-3}$ pascal for 26 hrs. The molecular sieve after impregnation was dried at 70° C. for 30 hrs and calcined at 650° C. for 2 hrs so as to obtain a modified molecular sieve.

Ferric citrate, manganese oxalate, copper sulfate, and potassium carbonate were weighed according to a weight ratio of iron:manganese:copper:potassium=18:6:3:1 and dissolved in water to prepare a solution. A surfactant sodium lauryl sulfate having a weight accounting for 0.1 wt. % of a weight of the solution was added to the solution while stirring. The cerium modified-aluminosilicate molecular sieve SAPO-34 was weighed quantitatively according to a weight ratio of iron to the molecular sieve of 1:4. The solution was added to the molecular sieve under vacuum and uniformly mixed to yield a mixture. The mixture was then dried at 40° C. for 7 hrs and calcined at 400° C. for 8 hrs to yield a FTO catalyst C in a powder state, and specific components of the catalyst C were listed in Table 1. Evaluation process of the activity of the catalyst was the same as that of Example 1. The reaction results using the catalyst C were shown in Table 2 from which it was known that a conversion rate of CO was 94.7% and selectivity of the light olefin in light hydrocarbon (excluding methane) was 84.7%.

EXAMPLE 4

Praseodymium nitrate and an aluminosilicate molecular sieve SAPO-34 were weighed according to a weight ratio of praseodymium to the molecular sieve of 1:4. The molecular sieve was added to an ammonium sulfate solution having a concentration of 0.1 mol/L and a resulting mixture was refluxed at 80° C. for 5 hrs and then filtered. A filter residue was washed, dried, and calcined at 700° C. for 6 hrs to yield a hydrogen type-molecular sieve. Thereafter, the hydrogen type-molecular sieve was uniformly mixed with a praseodymium nitrate solution and then impregnated at 60° C. at the vacuum degree of $10^{-3}$ pascal for 22 hrs. The molecular sieve after impregnation was dried at 100° C. for 24 hrs and calcined at 500° C. for 5 hrs so as to obtain a modified molecular sieve.

Ferric oxalate, manganese sulfate, copper citrate, and potassium carbonate were weighed according to a weight ratio of iron:manganese:copper:potassium=39:10:9:2 and dissolved in water to prepare a solution. A surfactant sodium lauryl sulfate having a weight accounting for 0.1 wt. % of a weight of the solution was added to the solution while stirring. The praseodymium modified-aluminosilicate molecular sieve SAPO-34 was weighed quantitatively according to a weight ratio of iron to the molecular sieve of 39:40. The solution was added to the molecular sieve under vacuum and uniformly mixed to yield a mixture. The mixture was then dried at 60° C. for 6 hrs and calcined at 550° C. for 4 hrs to yield a FTO catalyst D in a powder state, and specific components of the catalyst D were listed in Table 1. Evaluation process of the activity of the catalyst was the same as that of Example 1. The reaction results using the catalyst D were shown in Table 2 from which it was known that a conversion rate of CO was 94.9% and selectivity of the light olefin in light hydrocarbon (excluding methane) was 88.8%.

EXAMPLE 5

Praseodymium nitrate and a molecular sieve ZSM-5 were weighed according to a weight ratio of praseodymium to the molecular sieve of 1:9. The molecular sieve was added to an ammonium nitrate solution having a concentration of 0.1 mol/L and a resulting mixture was refluxed at 80° C. for 5 hrs and then filtered. A filter residue was washed, dried, and calcined at 700° C. for 6 hrs to yield a hydrogen type-molecular sieve. Thereafter, the hydrogen type-molecular sieve was uniformly mixed with a praseodymium nitrate solution and then impregnated at 70° C. at the vacuum degree of $10^{-2}$ pascal for 20 hrs. The molecular sieve after impregnation was dried at 120° C. for 22 hrs and calcined at 600° C. for 3 hrs so as to obtain a modified molecular sieve.

Ferric citrate, manganese nitrate, copper oxalate, and potassium carbonate were weighed according to a weight ratio of iron:manganese:copper:potassium=11:3:2:1 and dissolved in water to prepare a solution. A surfactant sodium lauryl sulfate having a weight accounting for 0.1 wt. % of a weight of the solution was added to the solution while stirring. The praseodymium modified-molecular sieve ZSM-5 was weighed quantitatively according to a weight ratio of iron to the molecular sieve of 1:3. The solution was added to the molecular sieve under vacuum and uniformly mixed to yield a mixture. The mixture was then dried at 50° C. for 5 hrs and calcined at 600° C. for 7 hrs to yield a FTO catalyst E in a powder state, and specific components of the catalyst E were listed in Table 1. Evaluation process of the activity of the catalyst was the same as that of Example 1. The reaction results using the catalyst E were shown in Table 2 from which it was known that a conversion rate of CO was 93.3% and selectivity of the light olefin in light hydrocarbon (excluding methane) was 87.2%.

EXAMPLE 6

Praseodymium nitrate and a molecular sieve ZSM-5 were weighed according to a weight ratio of praseodymium to the molecular sieve of 1:19. The molecular sieve was added to an ammonium sulfate solution having a concentration of 0.1 mol/L and a resulting mixture was refluxed at 80° C. for 5 hrs and then filtered. A filter residue was washed, dried, and calcined at 700° C. for 6 hrs to yield a hydrogen type-molecular sieve. Thereafter, the hydrogen type-molecular sieve was uniformly mixed with a praseodymium nitrate solution and then impregnated at 40° C. at the vacuum degree of $10^{-1}$ pascal for 28 hrs. The molecular sieve after impregnation was dried at 80° C. for 26 hrs and calcined at 700° C. for 1 hr so as to obtain a modified molecular sieve.

Ferric sulfate, manganese nitrate, copper citrate, and potassium carbonate were weighed according to a weight ratio of iron:manganese:copper:potassium=18:6:3:1 and dissolved in water to prepare a solution. A surfactant sodium lauryl sulfate having a weight accounting for 0.1 wt. % of a weight of the solution was added to the solution while stirring. The praseodymium modified-molecular sieve ZSM-5 was weighed quantitatively according to a weight ratio of iron to the molecular sieve of 1:4. The solution was added to the molecular sieve under vacuum and uniformly mixed to yield a mixture. The mixture was then dried at 70° C. for 3 hrs and calcined at 450° C. for 6 hrs to yield a FTO catalyst F in a powder state, and specific components of the catalyst F were listed in Table 1. Evaluation process of the activity of the catalyst was the same as that of Example 1. The reaction results using the catalyst F were shown in Table 2 from which it was known that a conversion rate of CO was 94.5% and selectivity of the light olefin in light hydrocarbon (excluding methane) was 85.6%.

EXAMPLE 7

Cerium nitrate, praseodymium nitrate, and an aluminosilicate molecular sieve SSZ-13 were weighed according to a weight ratio of cerium:praseodymium:molecular sieve=0.5:0.5:99. The molecular sieve was added to an ammonium nitrate solution having a concentration of 0.1 mol/L and a resulting mixture was refluxed at 80° C. for 5 hrs and then filtered. A filter residue was washed, dried, and calcined at 700° C. for 6 hrs to yield a hydrogen type-molecular sieve. Thereafter, the hydrogen type-molecular sieve was uniformly mixed with a cerium nitrate and praseodymium nitrate solution and then impregnated at 85° C. at the vacuum degree of $10^{-4}$ pascal for 24 hrs. The molecular sieve after impregnation was dried at 130° C. for 20 hrs and calcined at 550° C. for 6 hrs so as to obtain a modified molecular sieve.

Ferric oxalate, manganese nitrate, copper citrate, and potassium carbonate were weighed according to a weight ratio of iron:manganese:copper:potassium=15:10:5:5 and dissolved in water to prepare a solution. A surfactant sodium lauryl sulfate having a weight accounting for 0.1 wt. % of a weight of the solution was added to the solution while stirring. The cerium-praseodymium modified-aluminosilicate molecular sieve SSZ-13 was weighed quantitatively according to a weight ratio of iron to the molecular sieve of 3:13. The solution was added to the molecular sieve under vacuum and uniformly mixed to yield a mixture. The mixture was then dried at 65° C. for 4 hrs and calcined at 600° C. for 3 hrs to yield a FTO catalyst G in a powder state, and specific components of the catalyst G were listed in Table 1. Evaluation process of the activity of the catalyst was the same as that of Example 1. The reaction results using the catalyst G were shown in Table 2 from which it was known that a conversion rate of CO was 95.2% and selectivity of the light olefin in light hydrocarbon (excluding methane) was 88.5%.

EXAMPLE 8

Cerium nitrate, praseodymium nitrate, and an aluminosilicate molecular sieve SSZ-13 were weighed according to a weight ratio of cerium:praseodymium:molecular sieve=1:1:18. The molecular sieve was added to an ammonium sulfate solution having a concentration of 0.1 mol/L and a resulting mixture was refluxed at 80° C. for 5 hrs and then filtered. A filter residue was washed, dried, and calcined at 700° C. for 6 hrs to yield a hydrogen type-molecular sieve. Thereafter, the hydrogen type-molecular sieve was uniformly mixed with a cerium nitrate and praseodymium nitrate solution and then impregnated at 25° C. at the vacuum degree of $10^{-1}$ pascal for 30 hrs. The molecular sieve after impregnation was dried at 150° C. for 15 hrs and calcined at 700° C. for 6 hrs so as to obtain a modified molecular sieve.

Ferric nitrate, manganese nitrate, copper citrate, and potassium nitrate were weighed according to a weight ratio of iron:manganese:copper:potassium=35:1:5:4 and dissolved in water to prepare a solution. A surfactant sodium lauryl sulfate having a weight accounting for 0.1 wt. % of a weight of the solution was added to the solution while stirring. The cerium-praseodymium modified-aluminosilicate molecular sieve SSZ-13 was weighed quantitatively according to a weight ratio of iron to the molecular sieve of 7:11. The solution was added to the molecular sieve under vacuum and uniformly mixed to yield a mixture. The mixture was then dried at 30° C. for 8 hrs and calcined at 500° C. for 5 hrs to yield a FTO catalyst H in a powder state, and specific components of the catalyst H were listed in Table 1. Evaluation process of the activity of the catalyst was the same as that of Example 1. The reaction results using the catalyst H were shown in Table 2 from which it was known that a conversion rate of CO was 96.3% and selectivity of the light olefin in light hydrocarbon (excluding methane) was 89.3%.

EXAMPLE 9

Cerium nitrate, praseodymium nitrate, and an aluminosilicate molecular sieve SAPO-34 were weighed according to a weight ratio of cerium:praseodymium:molecular sieve=1:1:8. The molecular sieve was added to an ammonium nitrate solution having a concentration of 0.1 mol/L and a resulting mixture was refluxed at 80° C. for 5 hrs and then filtered. A filter residue was washed, dried, and calcined at 700° C. for 6 hrs to yield a hydrogen type-molecular sieve. Thereafter, the hydrogen type-molecular sieve was uniformly mixed with a cerium nitrate and praseodymium nitrate solution and then impregnated at 50° C. at the vacuum degree of $10^{-3}$ pascal for 26 hrs. The molecular sieve after impregnation was dried at 70° C. for 30 hrs and calcined at 650° C. for 2 hrs so as to obtain a modified molecular sieve.

Ferric citrate, manganese oxalate, copper sulfate, and potassium carbonate were weighed according to a weight ratio of iron:manganese:copper:potassium=20:10:5:2 and dissolved in water to prepare a solution. A surfactant sodium lauryl sulfate having a weight accounting for 0.1 wt. % of a weight of the solution was added to the solution while stirring. The cerium-praseodymium modified-aluminosilicate molecular sieve SAPO-34 was weighed quantitatively according to a weight ratio of iron to the molecular sieve of 20:63. The solution was added to the molecular sieve under vacuum and uniformly mixed to yield a mixture. The mixture was then dried at 40° C. for 7 hrs and calcined at 400° C. for 8 hrs to yield a FTO catalyst I in a powder state, and specific components of the catalyst I were listed in Table 1. Evaluation process of the activity of the catalyst was the same as that of Example 1. The reaction results using the catalyst I were shown in Table 2 from which it was known that a conversion rate of CO was 96.3% and selectivity of the light olefin in light hydrocarbon (excluding methane) was 87.6%.

EXAMPLE 10

Cerium nitrate and an aluminosilicate molecular sieve SAPO-34 were weighed according to a weight ratio of cerium to the molecular sieve of 1:4. The molecular sieve was added to an ammonium sulfate solution having a concentration of 0.1 mol/L and a resulting mixture was refluxed at 80° C. for 5 hrs and then filtered. A filter residue was washed, dried, and calcined at 700° C. for 6 hrs to yield a hydrogen type-molecular sieve. Thereafter, the hydrogen type-molecular sieve was uniformly mixed with a cerium nitrate solution and then impregnated at 60° C. at the vacuum degree of $10^{-3}$ pascal for 22 hrs. The molecular sieve after impregnation was dried at 100° C. for 24 hrs and calcined at 500° C. for 5 hrs so as to obtain a modified molecular sieve.

Ferric oxalate, manganese sulfate, copper citrate, and potassium carbonate were weighed according to a weight ratio of iron:manganese:copper:potassium=10:5:3:2 and dissolved in water to prepare a solution. A surfactant sodium lauryl sulfate having a weight accounting for 0.1 wt. % of a weight of the solution was added to the solution while stirring. The praseodymium modified-aluminosilicate molecular sieve SAPO-34 was weighed quantitatively according to a weight ratio of iron to the molecular sieve of 1: 8. The solution was added to the molecular sieve under vacuum and uniformly mixed to yield a mixture. The mixture was then dried at 60° C. for 6 hrs and calcined at 550° C. for 4 hr to yield a FTO catalyst J in a powder state, and specific components of the catalyst J were listed in Table 1. Evaluation process of the activity of the catalyst was the same as that of Example 1. The reaction results using the catalyst J were shown in Table 2 from which it was known that a conversion rate of CO was 95% and selectivity of the light olefin in light hydrocarbon (excluding methane) was 85.8%.

EXAMPLE 11

Praseodymium nitrate and a molecular sieve ZSM-5 were weighed according to a weight ratio of praseodymium to the molecular sieve of 1:99. The molecular sieve was added to an ammonium nitrate solution having a concentration of 0.1 mol/L and a resulting mixture was refluxed at 80° C. for 5 hrs and then filtered. A filter residue was washed, dried, and calcined at 700° C. for 6 hrs to yield a hydrogen type-molecular sieve. Thereafter, the hydrogen type-molecular sieve was uniformly mixed with a praseodymium nitrate solution and then impregnated at 70° C. at the vacuum degree of $10^{-2}$ pascal for 20 hrs. The molecular sieve after impregnation was dried at 120° C. for 22 hrs and calcined at 600° C. for 3 hrs so as to obtain a modified molecular sieve.

Ferric citrate, manganese nitrate, copper oxalate, and potassium carbonate were weighed according to a weight ratio of iron:manganese:copper:potassium=23:1:9:7 and dissolved in water to prepare a solution. A surfactant sodium lauryl sulfate having a weight accounting for 0.1 wt. % of a weight of the solution was added to the solution while stirring. The praseodymium modified-molecular sieve ZSM-5 was weighed quantitatively according to a weight ratio of iron to the molecular sieve of 23:60. The solution was added to the molecular sieve under vacuum and uniformly mixed to yield a mixture. The mixture was then dried at 50° C. for 5 hrs and calcined at 600° C. for 7 hr to yield a FTO catalyst potassium in a powder state, and specific components of the catalyst potassium were listed in Table 1. Evaluation process of the activity of the catalyst was the same as that of Example 1. The reaction results using the catalyst potassium were shown in Table 2 from which it was known that a conversion rate of CO was 94.2% and selectivity of the light olefin in light hydrocarbon (excluding methane) was 86.3%.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A catalyst, comprising:
    an active component, the active component comprising iron, manganese, copper, and potassium; and
    a modified molecular sieve carrier, the modified molecular sieve carrier comprising a zeolite and a cerium salt and/or a praseodymium salt;
wherein:
    the zeolite is SSZ-13, SAPO-34, or ZSM-5; and
    the catalyst comprises between 10 and 35 wt. % of iron, between 1 and 20 wt. % of manganese, between 1 and 20 wt. % of copper, between 1 and 10 wt. % of potassium, and between 40 and 80 wt. % of the molecular sieve carrier.

2. The catalyst of claim 1, wherein the cerium salt and/or the praseodymium salt account(s) for between 1 and 20 wt. % of the modified molecular sieve carrier.

3. The catalyst of claim 1, wherein the cerium salt and/or the praseodymium salt account(s) for between 10 and 20 wt. % of the modified molecular sieve carrier.

* * * * *